(12) United States Patent
Liu et al.

(10) Patent No.: US 12,728,217 B2
(45) Date of Patent: Sep. 8, 2026

(54) VENTILATION THERAPY DEVICE

(71) Applicant: BMC MEDICAL CO., LTD., Beijing (CN)

(72) Inventors: Lijun Liu, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 627 days.

(21) Appl. No.: 18/257,505

(22) PCT Filed: Nov. 24, 2021

(86) PCT No.: PCT/CN2021/132663

§ 371 (c)(1),
(2) Date: Jun. 14, 2023

(87) PCT Pub. No.: WO2022/142881

PCT Pub. Date: Jul. 7, 2022

(65) Prior Publication Data

US 2024/0033454 A1 Feb. 1, 2024

(30) Foreign Application Priority Data

Dec. 28, 2020 (CN) ........................ 202011582855.1

(51) Int. Cl.
*A61M 16/00* (2006.01)
*A61L 2/06* (2006.01)
(Continued)

(52) U.S. Cl.
CPC ........... *A61M 16/0003* (2014.02); *A61L 2/06* (2013.01); *A61M 16/16* (2013.01);
(Continued)

(58) Field of Classification Search
CPC .. A61M 16/0003; A61M 16/16; A61M 16/00; A61M 16/0066; A61M 16/107;
(Continued)

(56) References Cited

U.S. PATENT DOCUMENTS

2008/0310994 A1* 12/2008 O'Donnell ................ A61L 2/24
128/203.14

FOREIGN PATENT DOCUMENTS

AT 391934 B 12/1990
CN 101325979 A 12/2008
(Continued)

OTHER PUBLICATIONS

Extended European Search Report dated Mar. 11, 2024 for European Patent Application No. 21913623.1.

*Primary Examiner* — Ophelia A Hawthorne
(74) *Attorney, Agent, or Firm* — Volpe Koenig

(57) ABSTRACT

A ventilation therapy device comprising: a main machine used for producing a therapeutic gas and comprising a main machine air inlet and a main machine air outlet; and a disinfection apparatus, the disinfection apparatus used for producing a high-temperature disinfecting gas, the disinfection apparatus communicated with the main machine air inlet or the main machine air outlet so as to introduce the high-temperature disinfecting gas into the main machine. By providing the disinfection apparatus communicated with the main machine, the ventilation therapy device can perform all-around disinfection on the entire air passage of the main machine by means of the high-temperature disinfecting gas produced by the disinfection apparatus, the disinfection is dead-corner-free, residue-free, high in safety, and low in cost, so that the problem of a risk of a germ presenting inside the ventilation therapy device when the ventilation therapy device is used by a patient can be thoroughly solved.

19 Claims, 9 Drawing Sheets

(51) Int. Cl.
*A61M 16/16* (2006.01)
*A61L 103/15* (2026.01)

(52) U.S. Cl.
CPC ........ *A61L 2103/15* (2026.01); *A61L 2202/11* (2013.01); *A61M 2209/10* (2013.01)

(58) Field of Classification Search
CPC ........... A61M 2209/10; A61M 2205/75; A61L 2202/11; A61L 2202/14; A61L 2103/15
See application file for complete search history.

(56) References Cited

FOREIGN PATENT DOCUMENTS

| | | | |
|---|---|---|---|
| CN | 101332305 | A | 12/2008 |
| CN | 104606761 | A | 5/2015 |
| CN | 104879845 | A | 9/2015 |
| CN | 208405462 | U | 1/2019 |
| CN | 208770503 | U | 4/2019 |
| CN | 110652638 | A | 1/2020 |
| CN | 111450332 | A | 7/2020 |
| CN | 112587775 | A | 4/2021 |
| CN | 214807562 | U | 11/2021 |
| CN | 215024285 | U | 12/2021 |
| CN | 215133778 | U | 12/2021 |
| KR | 20100000633 | U | 1/2010 |
| KR | 10-2011-0108509 | A | 10/2011 |
| WO | 02065972 | A2 | 8/2002 |
| WO | 2012068131 | A1 | 5/2012 |

* cited by examiner 332
333
3311
3313
332
3312
3112
3121
311
313
3111

VENTILATION THERAPY DEVICE

This application is a 35 U.S.C. § 371 national stage of International Application No. PCT/CN2021/132663, which was filed Nov. 24, 2021 and claims the benefit of Chinese Patent Application No. 202011582855.1, filed on Dec. 28, 2020, both of which are incorporated herein by reference as if fully set forth.

FIELD

The present disclosure relates to the technical field of disinfection of ventilation therapy devices, in particular to a ventilation therapy device.

BACKGROUND

The cleaning, disinfection and maintenance of ventilation therapy devices enable ventilation therapy devices to be applied safely and reliably in clinical applications and prolong the service life of the ventilation therapy devices, and are tasks that can be executed seriously for ventilation therapy device users and clinical engineers. In order to prevent ventilation therapy devices from being contaminated by microorganisms, the components that are repeatedly used on ventilation therapy devices can be disinfected frequently, besides arranging filtering means on ventilation therapy devices.

At present, the disinfection of ventilation therapy devices is usually carried out with existing disinfection methods, for example, the external surfaces, touchable and manipulatable buttons/knobs of a ventilation therapy device, and the water tank of the humidifier of the ventilation therapy device are sterilized by means of ethylene oxide, hydrogen peroxide plasma, low-temperature formaldehyde vapor, peroxyacetic acid, alkaline glutaric dialdehyde, or ultraviolet light, etc.

However, in a ventilation therapy device, which is usually worn by a patient for a long time, there are a possibility and a risk of germs breeding in the entire gas channel from the gas inlet to the gas outlet during long-time use. If the patient uses a ventilation therapy device with germs in the gas passage, the ventilation therapy device can't relieve respiratory diseases, and may cause new diseases, leading to a result opposite to the wish of the patient. Moreover, most of the existing sterilization methods have a risk of residues after the disinfection, and the device can't be used again until it passes professional tests, which involve complicated operations, cumbersome procedures, high costs, and potential safety hazards.

SUMMARY

To solve the above problems, the present disclosure provides a ventilation therapy device, which can disinfect itself, has no residue, high safety, simple and easy operation, and a low cost.

To attain the above object, the present disclosure provides a ventilation therapy device, which comprises:

- a main machine that is configured to generate a therapeutic gas and has a main machine gas inlet and a main machine gas outlet; and
- a disinfection apparatus that is configured to generate a high-temperature disinfecting gas, and is communicated with the main machine gas inlet or the main machine gas outlet to introduce the high-temperature disinfecting gas into the main machine.

Optionally, the ventilation therapy device comprises a disinfection pipeline, the two ends of which are detachably connected to and communicated with the main machine and the disinfection apparatus respectively, so that the disinfection pipeline forms a channel for the high-temperature disinfecting gas to circulate together with the main machine and the disinfection apparatus.

Optionally, the ventilation therapy device comprises a humidifier, which is configured to humidify the therapeutic gas, and has a humidifier gas inlet and a humidifier gas outlet, wherein the humidifier gas inlet is communicated with the main machine gas outlet, and the disinfection apparatus is communicated with the humidifier to introduce the high-temperature disinfecting gas into the humidifier.

Optionally, the disinfection apparatus comprises a first power unit, a heating unit, and a gas transfer unit, wherein the first power unit is configured to supply a gas to the gas transfer unit, the heating unit is arranged between the first power unit and the gas transfer unit to heat the gas to form the high-temperature disinfecting gas, and the gas transfer unit is communicated with the main machine and the humidifier.

Optionally, the first power unit comprises a fan having a first fan gas inlet and a first fan gas outlet;

The gas transfer unit comprises a transfer case, which comprises a transfer cavity, a transfer case gas inlet and a transfer case gas outlet that are communicated with the transfer cavity, wherein the transfer case gas inlet is communicated with the first fan gas outlet, the transfer case gas outlet is communicated with the main machine gas outlet and the humidifier gas inlet, or is communicated with one of the main machine gas inlet and the humidifier gas outlet; and

- the heating unit comprises a heating element, which is arranged on a communication passage between the first fan gas outlet and the transfer case gas outlet.

Optionally, the first power unit comprises a shell, which comprises a mounting cavity, a shell gas inlet and a shell gas outlet that are communicated with the mounting cavity, wherein the first fan and the heating unit are mounted in the mounting cavity, the shell gas inlet corresponds to and is communicated with the first fan gas inlet, and the shell gas outlet corresponds to and is communicated with the first fan gas outlet and the transfer case gas inlet.

Optionally, the heating unit comprises a mounting cylinder, wherein one end of the mounting cylinder is hermetically connected to the first fan gas outlet, and the other end of the mounting cylinder is hermetically connected to the transfer case gas inlet, and the heating element is mounted in the mounting cylinder.

Optionally, the heating unit comprises a check valve mounted in the mounting cylinder.

Optionally, the main machine comprises a main machine connector, the first power unit comprises a power connector that can be electrically connected to an external power source or the main machine connector to supply power to the first power unit and the heating unit.

Optionally, the main machine comprises a main machine case having a cavity and a second power unit arranged in the cavity, and the main machine gas inlet and the main machine gas outlet are arranged on the main machine case and communicated with the cavity.

Optionally, the humidifier comprises a humidifier shell having a humidifying cavity, and the humidifier gas inlet and the humidifier gas outlet are arranged on the humidifier shell and communicated with the humidifying cavity.

Optionally, the second power unit comprises a second fan having a second fan gas inlet and a second fan gas outlet, wherein the second fan gas inlet corresponds to and is communicated with the main machine gas inlet, and the second fan gas outlet corresponds to and is communicated with the main machine gas outlet.

Optionally, the ventilation therapy device comprises a control unit configured to control the operation of the first power unit, the second power unit and the heating unit.

Optionally, the main machine comprises a filter mounted at the main machine gas inlet.

Optionally, the ventilation therapy device comprises a throttling unit arranged at the main machine gas inlet and/or the humidifier gas outlet.

Optionally, the throttling unit comprises a throttler, which can be connected to the main machine gas inlet or the humidifier gas outlet to throttle the flow rate of the high-temperature disinfecting gas discharged via the main machine gas inlet or the humidifier gas outlet.

Optionally, the throttling unit comprises a protector, which can be connected to the main machine gas inlet or the humidifier gas outlet.

The ventilation therapy device in the present disclosure is provided with a disinfection apparatus communicated with the main machine, the high-temperature disinfecting gas generated by the disinfection apparatus can disinfect the entire gas channel of the main machine comprehensively and thoroughly, and leaves no residue after the disinfection, and the disinfection is highly safe, has a low cost, and can eliminate the risk of the existence of germs in the ventilation therapy device when the ventilation therapy device is used by a patient.

Other features and advantages of the present disclosure will be further detailed in the following embodiments.

BRIEF DESCRIPTION OF THE DRAWINGS

The accompanying drawings, which constitute a part of the present disclosure, are provided to facilitate further understanding the present disclosure; the illustrative embodiments and associated description in the present disclosure are provided to explain the present disclosure, and shall not be deemed as constituting any undue limitation to the present disclosure. In the figures.

REFERENCE NUMBERS

Figure 1:
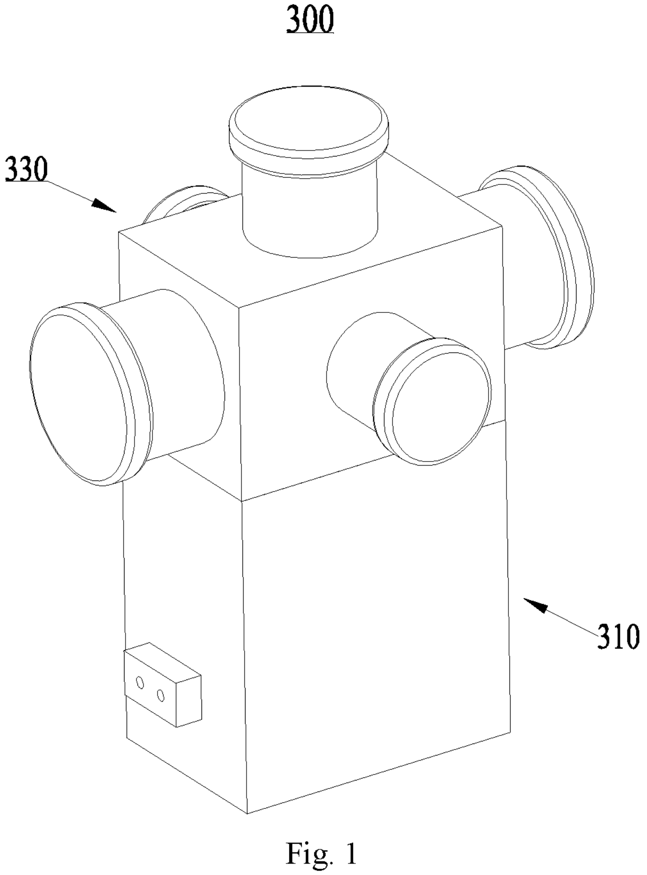
FIG. 1 is an isometric view of an embodiment of the disinfection apparatus in the present disclosure.

100—main machine, 110—main machine case, 111—main machine gas inlet, 112—main machine gas outlet, 113—cavity, 120—second fan, 121—second fan gas inlet, 122—second fan gas outlet, 130—filter, 140—stopper, 150—main machine connector;

200—humidifier, 210—humidifier shell, 211—humidifier gas inlet, 212—humidifier gas outlet, 213—humidifying cavity, 220—guide plate;

300—disinfection apparatus, 310—first power unit, 311—first fan, 3111—first fan gas inlet, 3112—first fan gas outlet, 312—shell, 3121—mounting cavity, 3122—shell gas inlet, 3123—shell gas outlet, 313—power connector, 320—heating unit, 321—heating element, 322—mounting cylinder, 323—check valve, 330—gas transfer unit, 331—transfer case, 3311—transfer cavity, 3312—transfer case gas inlet, 3313—transfer case gas outlet, 332—seal plug, 333—first gas monitor;

400—throttling unit, 410—throttler, 420—protector, 421—protective cylinder, 422—intercepting grille, 430—second gas monitor;

500—disinfection pipeline.

DETAILED DESCRIPTION

Some embodiments of the present disclosure will be detailed below with reference to the accompanying drawings. It needs to be understood that the embodiments described herein are only provided to describe and explain the present disclosure, but are not intended to constitute any limitation to the present disclosure.

Unless otherwise specified in the present disclosure, the terms that denote the directions or orientations, such as “top”, “bottom”, “left”, “right”, “front”, “back”, etc., usually refer to the directions or orientations as indicated in the figures; “inside” and “outside” usually refer to inside and outside with respect to the outlines of the components.

In one aspect, the present disclosure provides a disinfection apparatus 300, which comprises a first power unit 310, a heating unit 320 and a gas transfer unit 330, wherein the first power unit 310 is configured to supply a gas to the gas transfer unit 330, the heating unit 320 is arranged between the first power unit 310 and the gas transfer unit 330 to heat the gas to form a high-temperature disinfecting gas, and the gas transfer unit 330 is configured to introduce the high-temperature disinfecting gas into the gas channel of a device to be disinfected.

The device to be disinfected may be any device that has a gas channel and is to be disinfected, such as a ventilation therapy device. The heating unit 320 can heat the gas from the first power unit 310 to form a high-temperature disinfecting gas, then the high-temperature disinfecting gas enters the gas transfer unit 330 and is transferred by the gas transfer unit 330 to the gas channel of the device to be disinfected, so as to disinfect the entire gas channel. The gas provided by the first power unit 310 may be air, and the high-temperature disinfecting gas may be hot and dry air accordingly.

The disinfection apparatus 300 in the present disclosure can disinfect the entire gas channel comprehensively and thoroughly by utilizing a hot and dry gas, leaves no residue after the disinfection, and is highly safe, is easy to operate, and has a low cost, when the disinfection apparatus is used to disinfect the gas channel of the ventilation therapy device, the risk of the existence of germs inside the ventilation therapy device when the ventilation therapy device is used by a patient can be eliminated.

Some embodiments of the first power unit 310, the heating unit 320 and the gas transfer unit 330 will be detailed below in connection with the accompanying drawings respectively. It needs to be noted that the first power unit 310, the heating unit 320 and the gas transfer unit 330 are not limited to the embodiments to be described below, but may also be other embodiments that can realize the above functions.

Figures 5, 6:
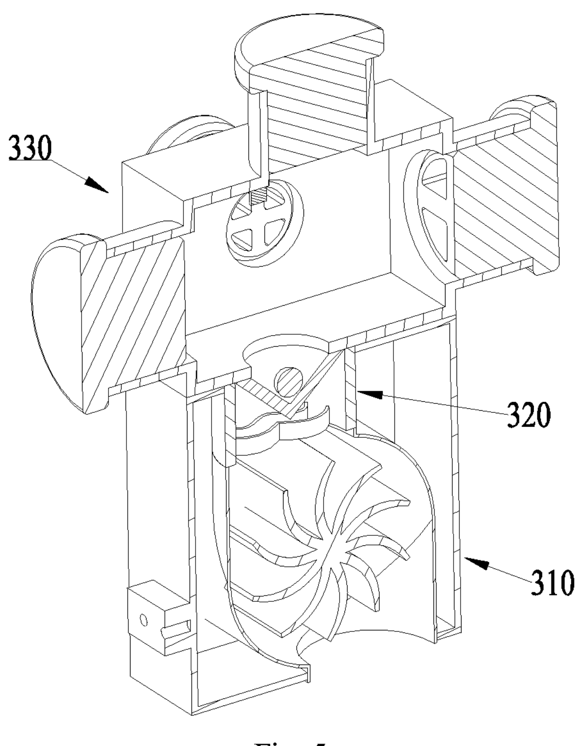
FIG. 5 is a longitudinal sectional view of the disinfection apparatus in FIG. 1.
FIG. 6 is a front view of the disinfection apparatus in FIG. 5, in which one transfer case gas outlet is open.

According to an embodiment of the first power unit 310 in the present disclosure, the first power unit 310 may comprise a first fan 311, which has a first fan gas inlet 3111 and a first fan gas outlet 3112 (see FIG. 6).

Figure 3:
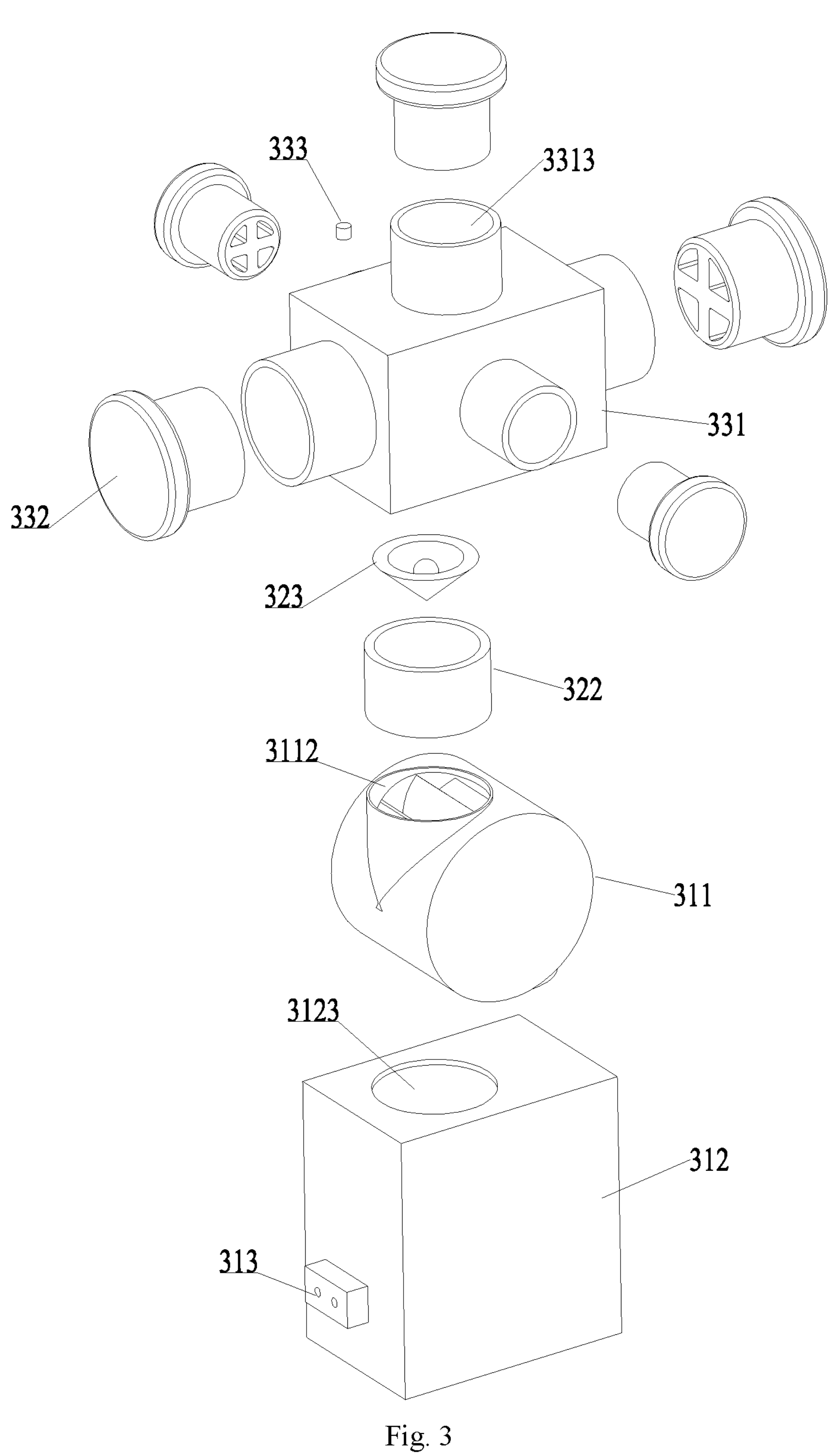
FIG. 3 is an exploded view of the disinfection apparatus in FIG. 1.
Figure 4:
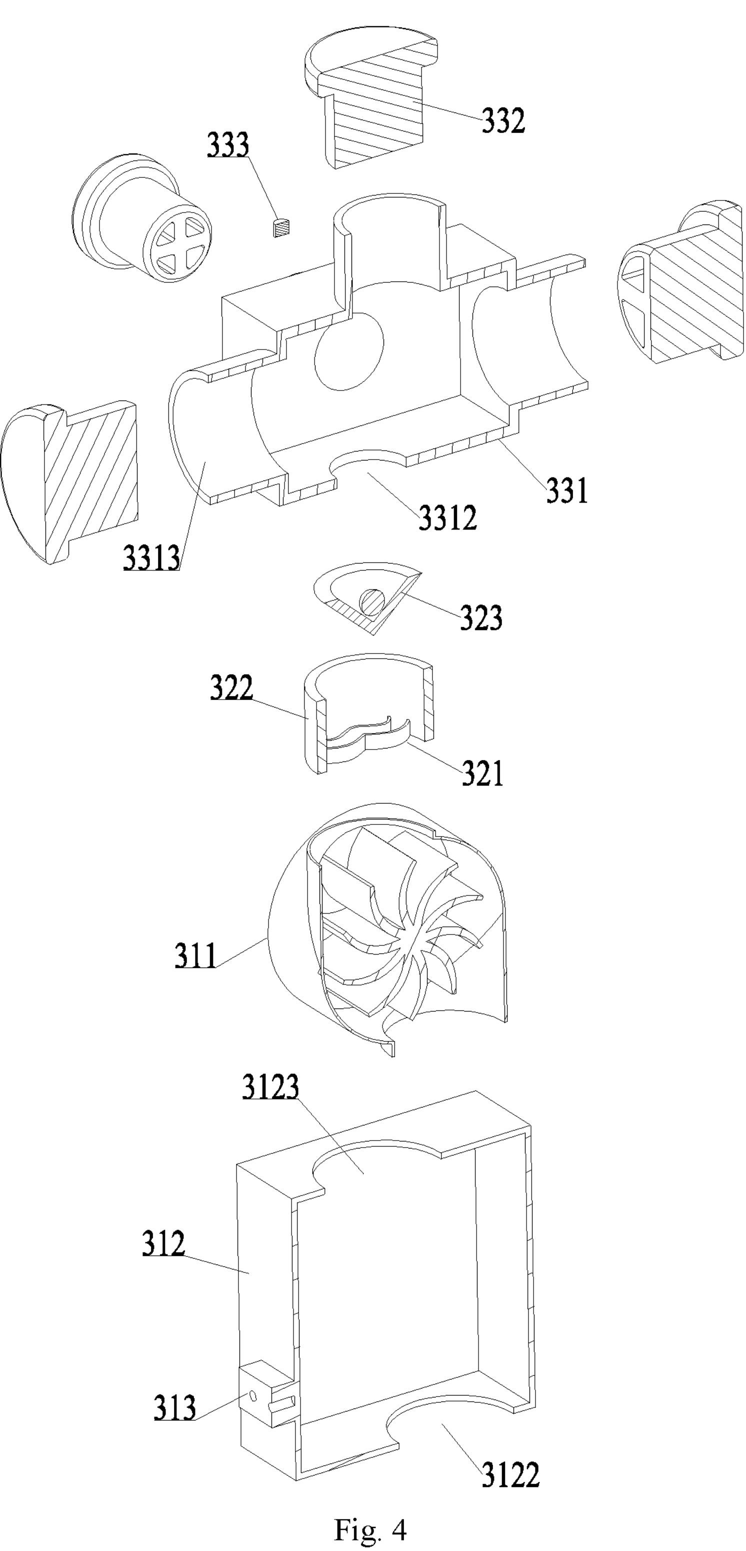
FIG. 4 is a longitudinal sectional view of the disinfection apparatus in FIG. 3.

Furthermore, to facilitate the fitting and mounting of the first fan 311 with other structures and protect the first fan 311, as shown in FIGS. 3-5, the first power unit 310 may further comprise a shell 312, which comprises a mounting cavity 3121, and a shell gas inlet 3122 and a shell gas outlet 3123 that are communicated with the mounting cavity 3121, the first fan 311 may be mounted in the mounting cavity 3121, the first fan gas inlet 3111 corresponds to and is communicated with the shell gas inlet 3122, and the first fan gas outlet 3112 corresponds to and is communicated with the shell gas outlet 3123. Wherein, the shell 312 may be in any appropriate shape. As shown in FIG. 6, the first fan gas inlet 3111 may extend out of the shell gas inlet 3122 to improve the gas supply efficiency. Of course, a filter may be arranged at the first fan gas inlet 3111 or the shell gas inlet 3122 to filter the incoming gas.

Figure 2:
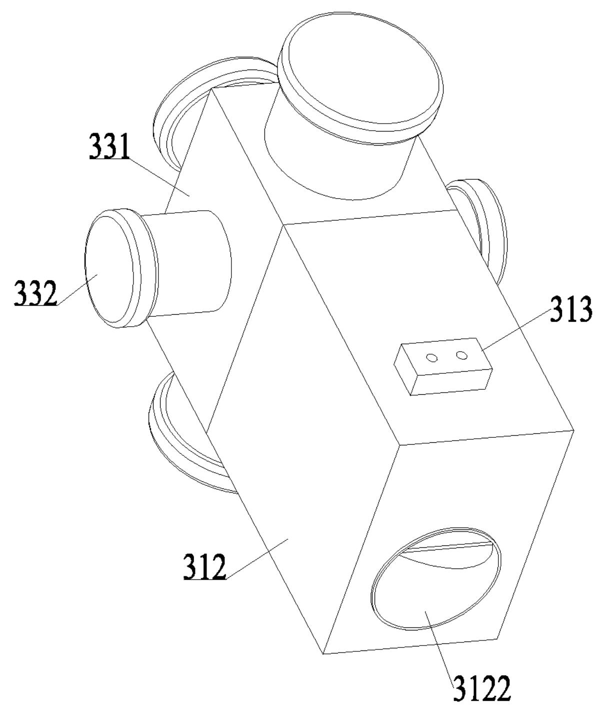
FIG. 2 is an isometric view of the disinfection apparatus in FIG. 1 when viewed from another viewing angle.

In addition, the first power unit 310 may further comprise a power connector 313, which may be connected to an external power source to supply power to the first fan 311. The power connector 313 may be mounted on the shell 312, as shown in FIGS. 1 and 2. Of course, the power connector 313 may also be used to supply power to the heating unit 320. The power connector 313 may be any type of connector in the prior art, such as a fixed connector or a connector with a cable plug.

According to an embodiment of the gas transfer unit 330 in the present disclosure, as shown in FIGS. 3-5, the gas transfer unit 330 may comprise a transfer case 331, which comprises a transfer cavity 3311, and a transfer case gas inlet 3312 and a transfer case gas outlet 3313 that are communicated with the transfer cavity 3311. The transfer case gas inlet 3312 is communicated with the first fan gas outlet 3112, and the transfer case gas outlet 3313 is communicated with the gas channel of the device to be disinfected.

The transfer case 331 may be in any shape. To enable simultaneous disinfection of a plurality of devices to be disinfected, the transfer case 331 may comprise a plurality of transfer case gas outlets 3313, each of which may be communicated with a device to be disinfected. Specifically, for example, as shown in FIG. 1, the transfer case 331 may be a square case, and the front side, back side, left side, right side and top side of the transfer case 331 may be provided with a transfer case gas outlet 3313 superior respectively.

The plurality of transfer case gas outlets 3313 may be in the same shape and dimensions, or may be in different shapes and dimensions so that they can be fitted with devices with different sizes of standard interfaces. Of course, in actual applications, each transfer case gas outlet 3313 may be provided with an adapter having specific diameter change or a one-to-many adapter, so as to connect one or more devices with different pipe diameters.

Furthermore, the gas transfer unit 330 may further comprise seal plugs 332, which may be detachably plugged in the transfer case gas outlets 3313. Wherein, the number of the seal plugs 332 may be equal to the number of the transfer case gas outlets 3313.

During use, the seal plug 332 of a transfer case gas outlet 3313 that is communicated with a device to be disinfected may be removed, while the other transfer case gas outlets 3313 are still sealed by the seal plugs 332.

For example, in the embodiment shown in FIG. 6, when disinfecting one device to be disinfected, one of the transfer case gas outlets 3313 is opened, while the other transfer case gas outlets 3313 are still sealed with the seal plugs 332. The gas flow direction is indicated by the arrow in FIG. 6.

Figures 7, 8:
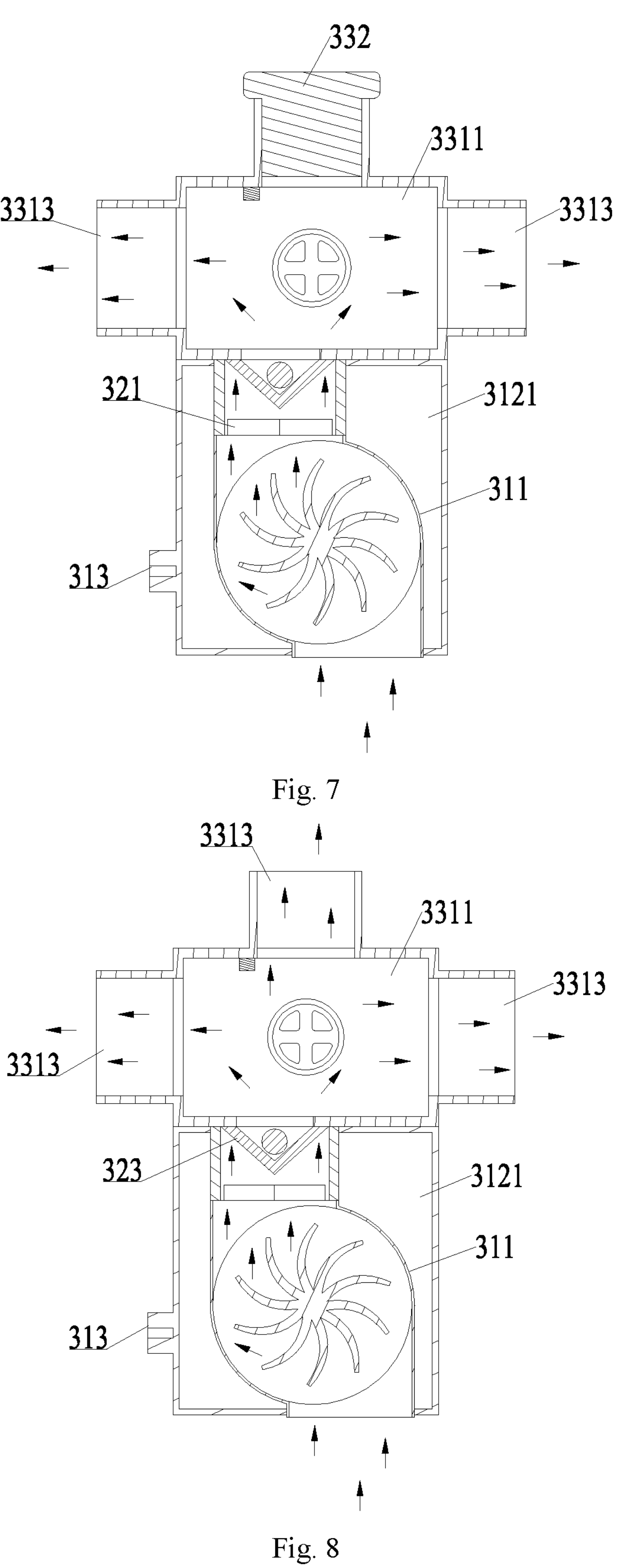
FIG. 7 is a front view of the disinfection apparatus in FIG. 5, in which two transfer case gas outlets are open.
FIG. 8 is a front view of the disinfection apparatus in FIG. 5, in which three transfer case gas outlets are open.
Figure 9:
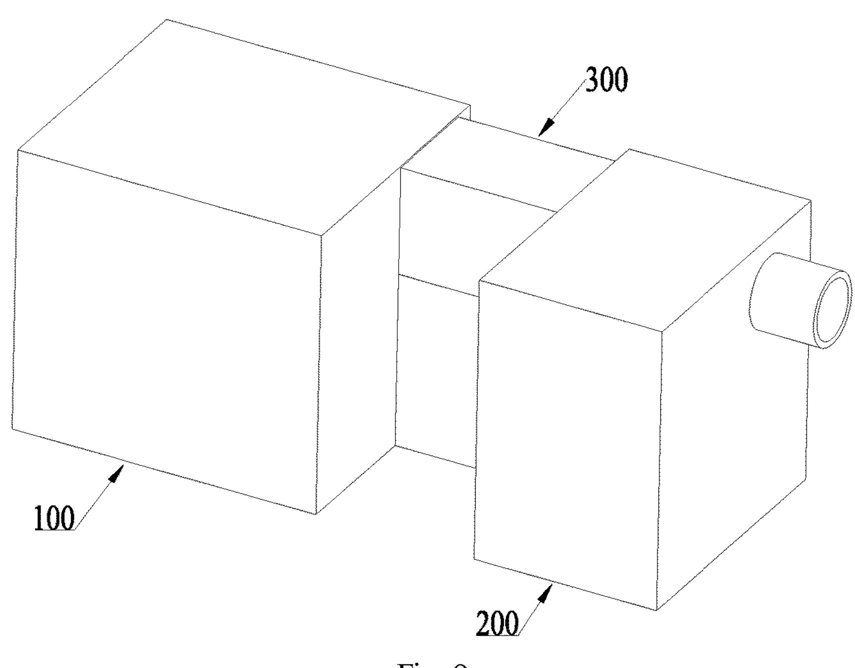
FIG. 9 is a schematic structural diagram of an embodiment of the ventilation therapy device in the present disclosure.
Figure 10:
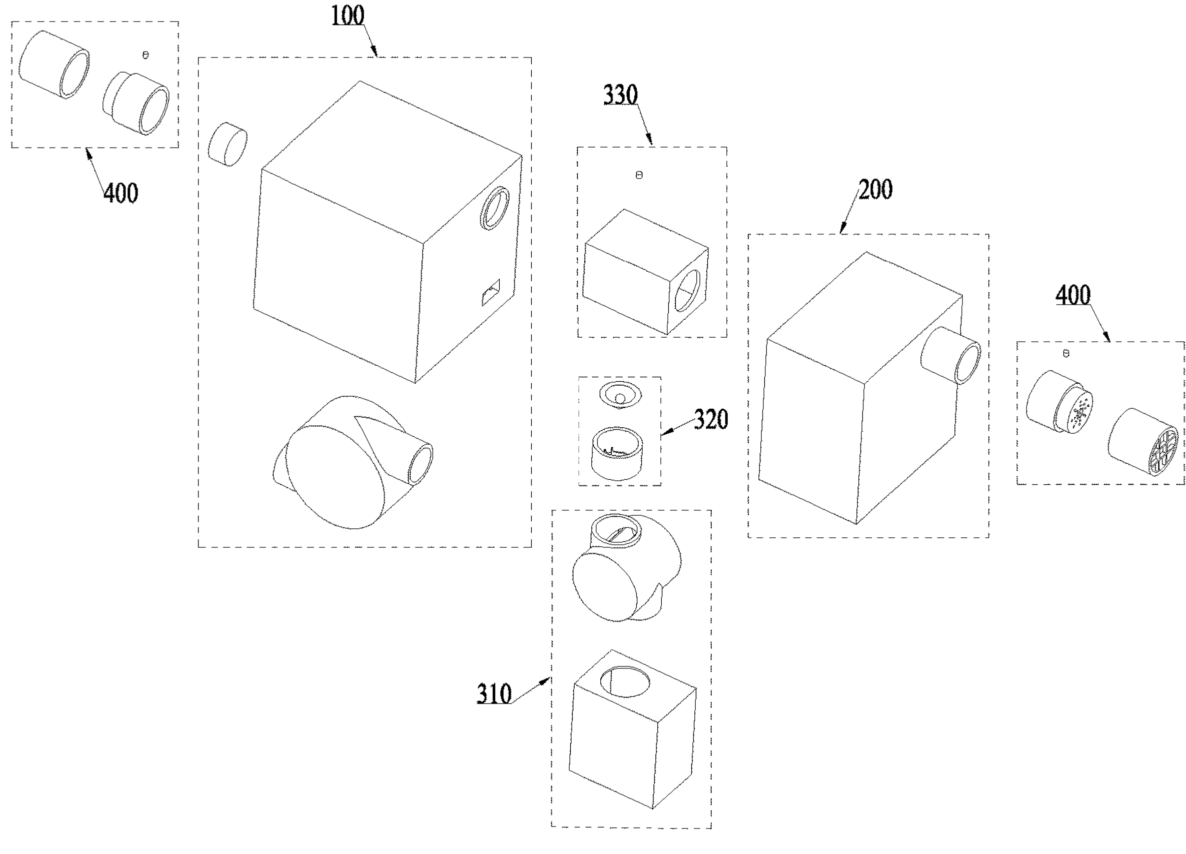
FIG. 10 is an exploded view of the ventilation therapy device in FIG. 9 after the throttling unit is mounted.

For example, in the embodiment shown in FIG. 7, when disinfecting two devices to be disinfected, two of the transfer case gas outlets 3313 are opened, while the other transfer case gas outlets 3313 are still sealed with the seal plugs 332. The gas flow direction is indicated by the arrow in FIG. 7.

For example, in the embodiment shown in FIG. 8, when disinfecting three devices to be disinfected, three of the transfer case gas outlets 3313 are opened, while the other transfer case gas outlets 3313 are still sealed with the seal plugs 332. The gas flow direction is indicated by the arrow in FIG. 8.

In the present disclosure, the seal plug 332 is preferably made of an elastically deformable and sealable material, such as silica gel or rubber. To facilitate the rapid fitting of the seal plug 332 to the transfer case gas outlet 3313, the insertion end of the seal plug 332 may be provided with a guide structure, such as a guide bevel. In addition, the insertion end of the seal plug 332 may be configured as a hollow structure to facilitate sealing, deformation and plugging. For the specific structure of the seal plug 332, please see the embodiment shown in FIG. 3.

According to an embodiment of the heating unit 320 in the present disclosure, the heating unit 320 may comprise a heating element 321, which is arranged on the communication path between the first fan gas outlet 3112 and the transfer case gas outlet 3313.

The heating element 321 may be understood as an element that can generate heat when it is powered, so as to heat up the gas. For example, the heating element 321 may be an element made of Fe—Cr—Al alloy, Ni—Cr alloy or copper wires. The heating element 321 may be in any appropriate shape, such as a plate shape (as shown in FIG. 4), a filament shape (i.e., a heating wire), and the like.

The temperature of the high-temperature disinfecting gas heated by the heating unit 320 is preferably not lower than 60° C., more preferably is 70-85° C.

Furthermore, to facilitate the mounting of the heating element 321, the heating unit 320 may further comprise a mounting cylinder 322, wherein one end of the mounting cylinder 322 is hermetically connected to the first fan gas outlet 3112, and the other end of the mounting cylinder 322 is hermetically connected to the transfer case gas inlet 3312, and the heating element 321 is mounted in the mounting cylinder 322 (see FIGS. 5 and 6). Of course, in other embodiments, the heating element 321 may be directly mounted at the transfer case gas inlet 3312 or the shell gas outlet 3123. The heating element 321 may be mounted on the communication path between the first fan gas outlet 3112 and the transfer case gas outlet 3313 in other ways.

In addition, the heating unit 320 may further comprise a check valve 323 to ensure that the gas flows unidirectionally from the first fan gas outlet 3112 to the transfer case gas inlet 3312. The check valve 323 may be mounted in the mounting cylinder 322. In the present disclosure, by integrating the heating element 321, the check valve 323 and the mounting cylinder 322 into an integral structure, they can be mounted, serviced, and fitted with other structures conveniently.

To make the disinfection apparatus 300 have a compact structure, a reasonable layout and a small footprint, as shown in FIG. 6, the heating unit 320 may also be mounted in the mounting cavity 3121 of the shell 312, and the upper end of the mounting cylinder 322 corresponds to and is communicated with the shell gas outlet 3123 and is communicated with the transfer case gas inlet 3312.

It needs to be noted that the communication between the gas inlets and the gas outlets in the present disclosure is sealed communication, so as to prevent gas leakage, ensure the high efficiency of gas supply and facilitate the control of the gas.

In the present disclosure, the disinfection apparatus 300 may further comprise a first gas monitor 333, which may be arranged in the transfer cavity 3311 to monitor the properties of the high-temperature disinfecting gas, i.e., temperature, humidity, pressure, flow, and flow rate, etc.

The first gas monitor 333 may be mounted at any position inside the transfer cavity 3311, and a plurality of first gas monitors 333 may be provided, for example, a first gas monitor 333 may be arranged at the gas inlet and the gas outlet of the transfer cavity 3311 respectively to monitor the properties of the incoming gas and the discharged gas.

In the present disclosure, the disinfection apparatus 300 may further comprise a control unit, first gas monitor 333 can transfer the monitored information to the control unit, and the control unit can control the operation of the heating element 321 and the first fan 311 according to the information monitored by the first gas monitor 333, so as to control the properties of the high-temperature disinfecting gas.

The disinfection apparatus 300 in the present disclosure may operate in two modes, i.e., a disinfection mode and a cooling mode.

Specifically, in the disinfection mode, the first fan 311 operates and provides the gas to the heating unit 320, the control unit controls the heating of the heating element 321 to heat the gas from the first fan 311 to form a high-temperature disinfecting gas, then the high-temperature disinfecting gas enters the transfer cavity 3311 via the check valve 323, and then enters the device to be disinfected via the transfer case gas outlet 3313 to perform high-temperature disinfection for the gas channel of the device to be disinfected.

When operating mode is switched from the disinfection mode to the cooling mode, the operation is the same as that in the disinfection mode, but the control unit stops the heating of the heating element 321, so that the gas at normal temperature from the first fan 311 directly enters the transfer cavity 3311, then enters into the gas channel of the device to be disinfected, to carry away the heat in the gas channel quickly and cool the entire gas channel, so that the patient can use the device to be disinfected conveniently in time.

The interface of the device to be disinfected to the transfer case gas outlet 3313 may be regarded as the gas inlet of the device to be disinfected, and the other end of the gas channel of the device to be disinfected may be regarded as the gas outlet. In actual applications, advantageously, a throttler, such as a flow valve, may be arranged at the gas outlet of the device to be disinfected to control the output flow and avoid losing the disinfection effect owing to excessively high flow.

In another aspect, the present disclosure provides a ventilation therapy device, which comprises the above-mentioned disinfection apparatus 300, and is configured to introduce the high-temperature disinfecting gas to the gas channel of the ventilation therapy device.

Specifically, the ventilation therapy device may comprise a main machine 100 and a disinfection apparatus 300. The main machine 100 is configured to generate a therapeutic gas, and has a main machine gas inlet 111 and a main machine gas outlet 112; the disinfection apparatus 300 is configured to generate a high-temperature disinfecting gas, and is communicated with the main machine gas inlet 111 or the main machine gas outlet 112 to introduce the high-temperature disinfecting gas to the main machine 100 and the humidifier 200.

Furthermore, the ventilation therapy device may further comprise a humidifier 200, which is configured to humidify the therapeutic gas, and has a humidifier gas inlet 211 and a humidifier gas outlet 212, wherein the humidifier gas inlet 211 is communicated with the main machine gas outlet 112. The disinfection apparatus 300 may be communicated with the humidifier 200 to introduce the high-temperature disinfecting gas into the humidifier 200.

In the above description, it can be understood that the disinfection apparatus 300 may be communicated with the main machine 100 and the humidifier 200 in three ways. In the first way, the disinfection apparatus 300 is communicated with the main machine 100, specifically, the disinfection apparatus 300 is communicated with the main machine gas inlet 111, the disinfection apparatus 300 is located at the side of the main machine 100, and the main machine gas outlet 112 is communicated with the humidifier gas inlet 211 directly; in the second way, the disinfection apparatus 300 is communicated with the humidifier 200, specifically, the disinfection apparatus 300 is communicated with the humidifier gas outlet 212, the disinfection apparatus 300 is located at the side of the humidifier 200, and the main machine gas outlet 112 is communicated with the humidifier gas inlet 211 directly (see FIG. 15); in the third way, the disinfection apparatus 300 is communicated with the main machine 100 and the humidifier 200, specifically, the disinfection apparatus 300 is communicated with the main machine gas outlet 112 and the humidifier gas inlet 211, that is to say, the disinfection apparatus 300 is arranged between the main machine 100 and the humidifier 200, and the main machine gas outlet 112 is communicated with the humidifier gas inlet 211 via the disinfection apparatus 300 indirectly (see FIG. 9, 11, 13 or 14).

Figure 13:
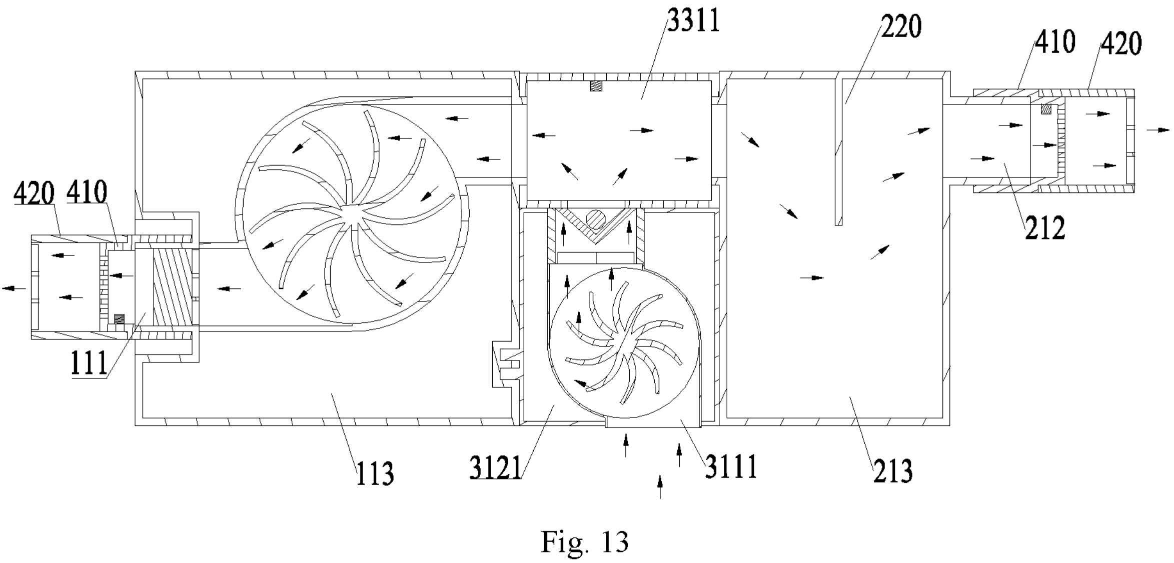
FIG. 13 is a front view of the ventilation therapy device in FIG. 11.
Figure 14:
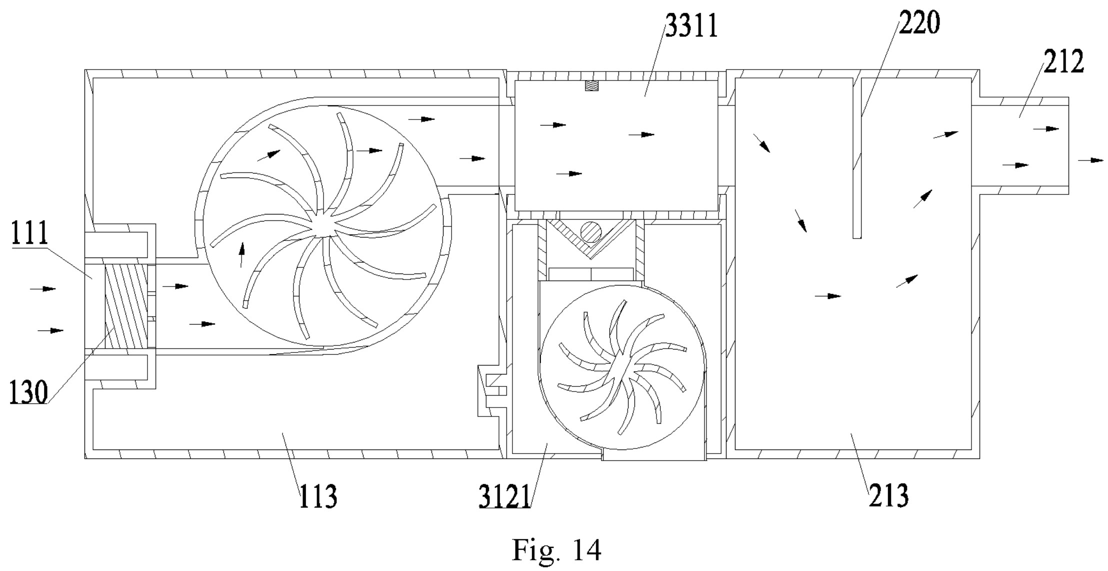
FIG. 14 is a sectional view of the ventilation therapy device in FIG. 9.

In the first way or second way described above, the disinfection apparatus 300 may have one transfer case gas outlet 3313 (see FIG. 15); in the third way, the disinfection apparatus 300 may have two transfer case gas outlets 3313, which are communicated with the main machine gas outlet 112 and the humidifier gas inlet 211 respectively (see FIG. 13 or 14).

Figure 12:
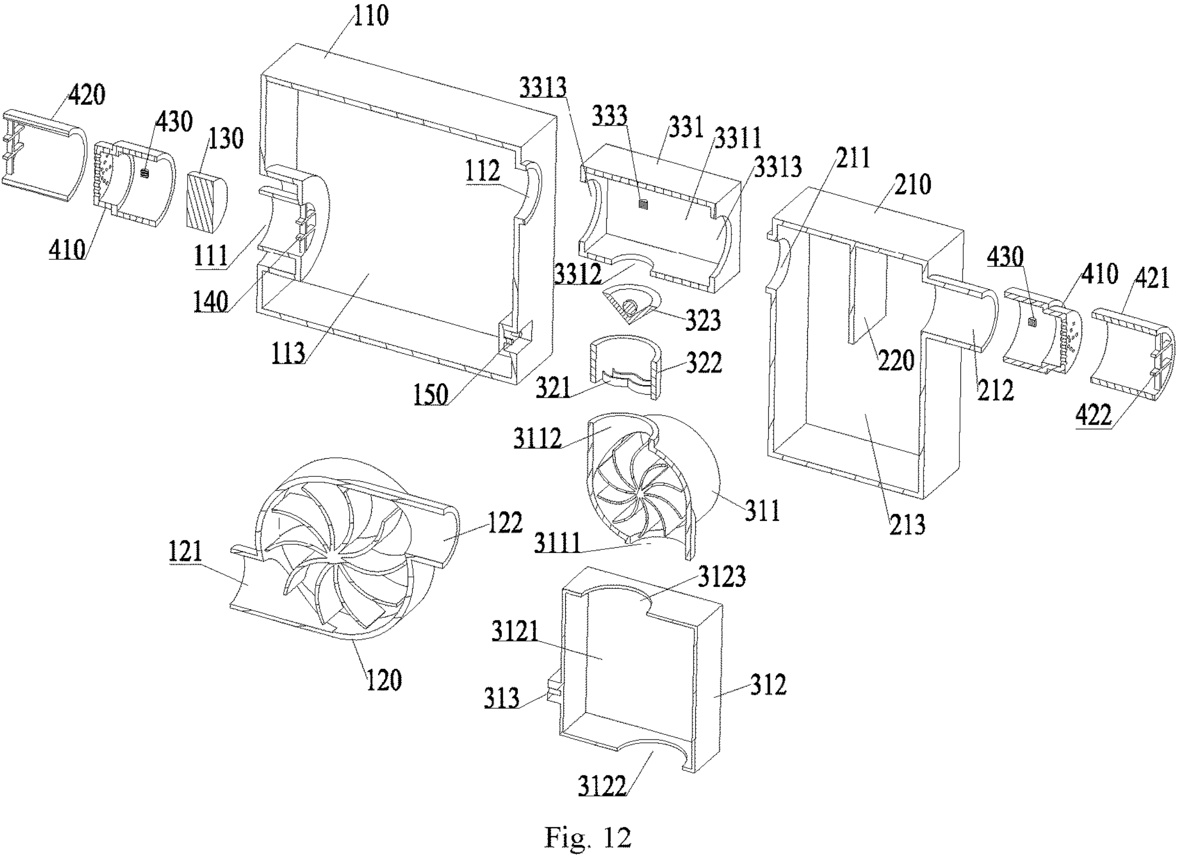
FIG. 12 is an exploded view of the ventilation therapy device in FIG. 11.

In the present disclosure, as shown in FIG. 12, the main machine 100 may comprise a main machine case 110 having a cavity 113 and a second power unit arranged in the cavity 113, and the main machine gas inlet 111 and the main machine gas outlet 112 are arranged on the main machine case 110 and are communicated with the cavity 113.

As shown in FIG. 13, the second power unit may comprise a second fan 120, which has a second fan gas inlet 121 and a second fan gas outlet 122, wherein the second fan gas inlet 121 corresponds to and is communicated with the main machine gas inlet 111, and the second fan gas outlet 122 corresponds to and is communicated with the main machine gas outlet 112.

During use, the second fan 120 can draw the gas outside the main machine gas inlet 111 into the second fan 120 via the main machine gas inlet 111 and the second fan gas inlet 121 sequentially, and discharge the gas out of the main machine 100 via the second fan gas outlet 122 and the main machine gas outlet 112 sequentially.

In the present disclosure, the main machine 100 may further comprise a main machine connector 150, which may be arranged on the main machine case 110, and may be electrically connected to an external power source to supply power to the second fan 120. The power connector 313 of the disinfection apparatus 300 may be connected to the main machine connector 150, so that the disinfection apparatus 300 is powered from the main machine connector 150 (see FIG. 13).

In the present disclosure, the main machine 100 may further comprise a filter 130 mounted at the main machine gas inlet 111. The filter 130 may be used to filter the gas entering the main machine 100, to prevent dust, foreign substances, and particles, etc. from entering the main machine 100 and contaminating the main machine 100 and finally entering the respiratory tract of the patient.

In view that the second fan 120 causes negative pressure at the second fan gas inlet 121 during use, a stop structure may be arranged at the main machine gas inlet 111 to retain the filter 130, so as to prevent the filter 130 from entering the second fan 120 under the action of the negative pressure. Specifically, as shown in FIGS. 12 and 13, for example, the stop structure may be a stopper 140 arranged on the inner side of the main machine gas inlet 111, and the stopper 140 has a through-hole for the gas to pass through.

In the present disclosure, as shown in FIGS. 12 and 13, the humidifier 200 comprises a humidifier shell 210 having a humidifying cavity 213, and the humidifier gas inlet 211 and the humidifier gas outlet 212 are arranged on the humidifier shell 210 and are communicated with the humidifying cavity 213.

The humidifying cavity 213 may store a liquid, such as water, to humidify the gas. To increase the through-flow area of the gas in the humidifying cavity 213 and thereby improve the humidification rate, a guide structure that can guide the gas to flow through a long flow path may be provided inside the humidifying cavity 213. Specifically, as shown in FIGS. 12-15, for example, the guide structure may be a guide plate 220, and the gas entering the humidifying cavity 213 via the humidifier gas inlet 211 may flow downward along the guide plate 220 and then flow upward to the humidifier gas outlet 212 and is discharged.

In the present disclosure, the ventilation therapy device may further comprise a control unit, which may be a control unit of the disinfection apparatus 300, and is configured to control the operation of the first power unit 310, the second power unit, and the heating unit 320. That is to say, the control unit is configured to control the operation of the entire ventilation therapy device.

In the present disclosure, the ventilation therapy device may further comprise a throttling unit 400, which may be arranged at the main machine gas inlet 111 and/or the humidifier gas outlet 212.

Figure 11:
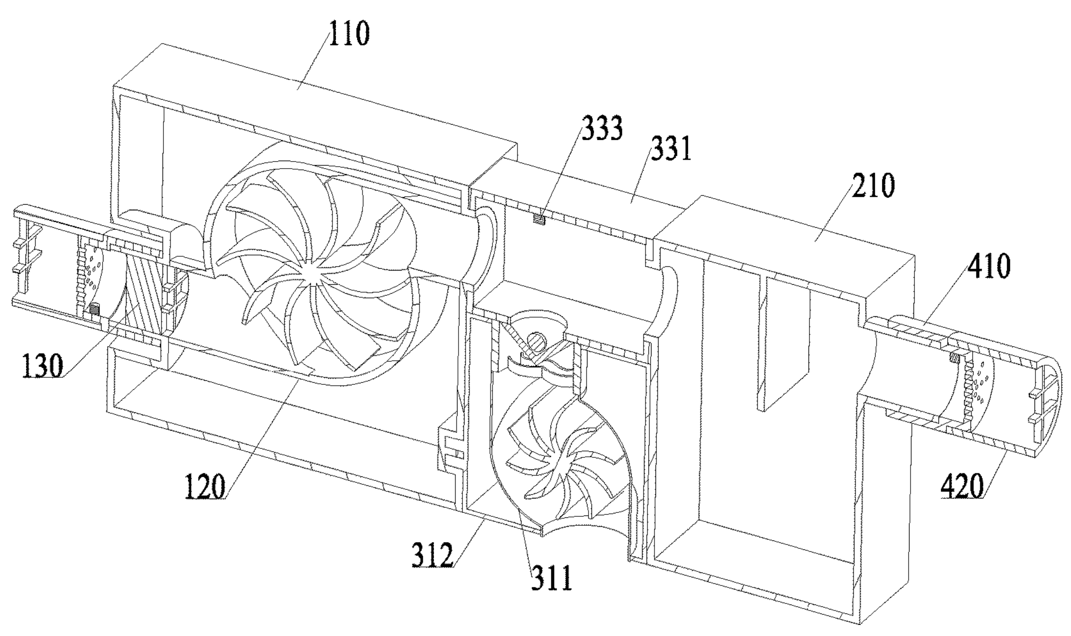
FIG. 11 is a sectional view of the ventilation therapy device in FIG. 9 after the throttling unit is mounted.

Specifically, if the disinfection apparatus 300 is communicated with the main machine gas inlet 111, the throttling unit 400 may be arranged at the humidifier gas outlet 212 to limit the gas flow rate at the humidifier gas outlet 212; if the disinfection apparatus 300 is communicated with the humidifier gas outlet 212, the throttling unit 400 may be arranged at the main machine gas inlet 111 to limit the gas flow rate at the main machine gas inlet 111 (see FIG. 15); if the disinfection apparatus 300 is connected between the main machine gas outlet 112 and the humidifier gas inlet 211, two throttling units 400 may be provided and arranged at the main machine gas inlet 111 and the humidifier gas outlet 212 respectively, to limit the gas flow rate at the main machine gas inlet 111 and the gas flow rate at the humidifier gas outlet 212 respectively (see FIG. 11).

The throttling unit 400 may comprise a throttler 410, which can be connected to the main machine gas inlet 111 or the humidifier gas outlet 212, to limit the gas flow rate of the high-temperature disinfecting gas discharged via the main machine gas inlet 111 or the humidifier gas outlet 212, so as to avoid losing the disinfection effect owing to an excessively high gas flow rate. The throttler 410 may be implemented in a variety of ways. For example, the throttler 410 may be a flow valve, or the cylindrical structure shown in FIGS. 11 and 12, wherein one end of the cylindrical structure may be inserted into the main machine gas inlet 111 or the humidifier gas outlet 212, and the other end of the cylindrical structure has an end wall with a plurality of vent holes.

Of course, in other embodiments, the ventilation therapy device may have no separate throttling unit 400; instead, the throttling function may be realized by means of the high gas resistance produced by the inherent structure of the main machine or the inherent structure of the humidifier.

To prevent user from injured by the high-temperature disinfecting gas discharged via the main machine gas inlet 111 or the humidifier gas outlet 212, the throttling unit 400 may comprise a protector 420, which can be connected to the main machine gas inlet 111 or the humidifier gas outlet 212. Of course, in the case that the throttler 410 employs the embodiment shown in FIGS. 11 and 12, the protector 420 may be mounted outside the throttler 410.

Specifically, as shown in FIGS. 11 and 12, the protector 420 may comprise a protective cylinder 421 sleeved outside the throttler 410.

Furthermore, to prevent fingers from entering the protective cylinder 421 or prevent other objects from entering the protective cylinder 421 and blocking the protective cylinder 421, the end of the protective cylinder 421 away from the throttler 410 may be provided with an intercepting grille 422.

In the present disclosure, the ventilation therapy device may further comprise a second gas monitor 430, which may be used to monitor the properties of the high-temperature disinfecting gas discharged via the main machine gas inlet 111 or the humidifier gas outlet 212, so as to control the operation of the disinfection apparatus in a better way.

In the present disclosure, the ventilation therapy device may further comprise a ventilation pipeline and a patient interface, wherein one end of the ventilation pipeline is connected to the patient interface, and the other end of the ventilation pipeline may be connected to the humidifier gas outlet 212 or the transfer case gas outlet 3313.

The ventilation therapy device in the present disclosure may have three operating modes, i.e., a therapy mode, a disinfection mode, and a cooling mode.

Specifically, as shown in FIG. 14, in the therapy mode, the first fan 311 and the check valve 323 are in an inactive state, and the second fan 120 operates, as indicated by the arrow in FIG. 14, the gas enters the second fan 120 via the main machine gas inlet 111 and the second fan gas inlet 121 sequentially, then enters the transfer cavity 3311 via the second fan gas outlet 122, the main machine gas outlet 112, and the left transfer case gas outlet 3313 sequentially, and then enters the humidifying cavity 213 for humidification via the right transfer case gas outlet 3313 and the humidifier gas inlet 211, the humidified gas enters the ventilation pipeline via the humidifier gas outlet 212, and finally enters the patient interface for the patient to inhale.

In the disinfection mode, as illustrated by the embodiment shown in FIG. 13, the second fan 120 is in an inactive state, the first fan 311 and the check valve 323 operate, and the heating element 321 generates heat, as indicated by the arrow in FIG. 13, the gas enters the first fan 311 via the first fan gas inlet 3111, then enters the mounting cylinder 322 via the first fan gas outlet 3113, is heated by the heating element 321 to form a high-temperature disinfecting gas, then the high-temperature disinfecting gas enters the transfer cavity 3311 via the check valve 323 and the transfer case gas inlet 3312 sequentially, then enters the second fan 120 and the humidifying cavity 213 via the left and right transfer case gas outlets 3313 respectively to carry out high-temperature disinfection for the main machine 100 and the humidifier 200, and then is discharged via the main machine gas inlet 111 and the humidifier gas outlet 212. Of course, in the case that the humidifier gas outlet 212 is connected to the ventilation pipeline and the patient interface, high-temperature disinfection may also be carried out for the ventilation pipeline and the patient interface.

Figure 15:
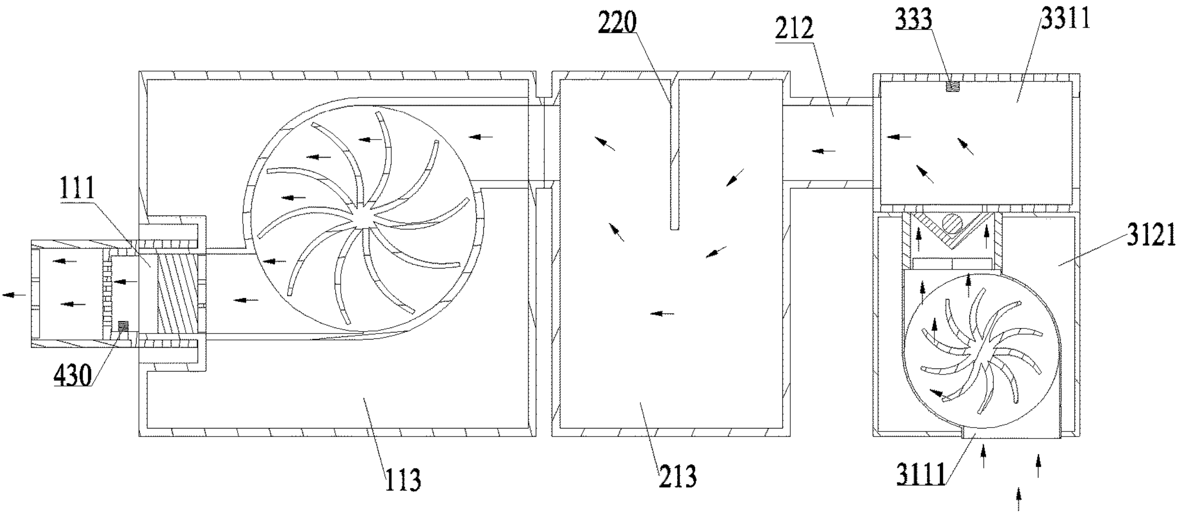
FIG. 15 is a sectional view of another embodiment of the ventilation therapy device in the present disclosure.

In the disinfection mode, as illustrated by the embodiment shown in FIG. 15, the second fan 120 is in an inactive state, the first fan 311 and the check valve 323 operate, and the heating element 321 generates heat, as indicated by the arrow in FIG. 15, the gas enters the first fan 311 via the first fan gas inlet 3111, then enters the mounting cylinder 322 via the first fan gas outlet 3113, is heated by the heating element 321 to form a high-temperature disinfecting gas, then the high-temperature disinfecting gas enters the transfer cavity 3311 via the check valve 323 and the transfer case gas inlet 3312 sequentially, then enters the humidifying cavity 213 via the transfer case gas outlet 3313 and the humidifier gas outlet 212 sequentially to carry out high-temperature disinfection for the humidifier 200, then the high-temperature disinfecting gas enters the second fan 120 via the humidifier gas inlet 211, the main machine gas outlet 112, and the second fan gas outlet 122 to carry out high-temperature disinfection for the main machine 100, and finally is discharged via the second fan gas inlet 121 and the main machine gas inlet 111 sequentially.

In the cooling mode, the heating element 321 doesn't generate heat, and the first fan 311 or the second fan 120 operates to draw the external gas at normal temperature into the ventilation therapy device, to carry away the heat inside the device quickly, so as to cool the entire device.

In actual use, the ventilation treatment device may be set so that the control unit activates the disinfection mode only if the humidifier gas outlet 212 is connected to the throttling unit 400, so as to prevent the humidifier gas outlet 212 without the throttling unit 400 from opening to the air or connected to the ventilation pipeline and causing injuries to the patient, such as scalding or scorching, etc.

With the above technical scheme, the entire gas channel inside the ventilation therapy device from the gas inlet of the ventilation therapy device to the gas outlet of the ventilation therapy device, through which the respiratory gas for the patient flows, can be disinfected comprehensively and thoroughly by the high-temperature disinfecting gas generated by the disinfection apparatus, and there is no residue after the disinfection. Thus, the risk of the existence of germs inside the ventilation therapy device when the ventilation therapy device is used by a patient can be eliminated.

In the present disclosure, the ventilation therapy device may be a ventilator or an oxygen therapy apparatus, or the like.

Figure 16:
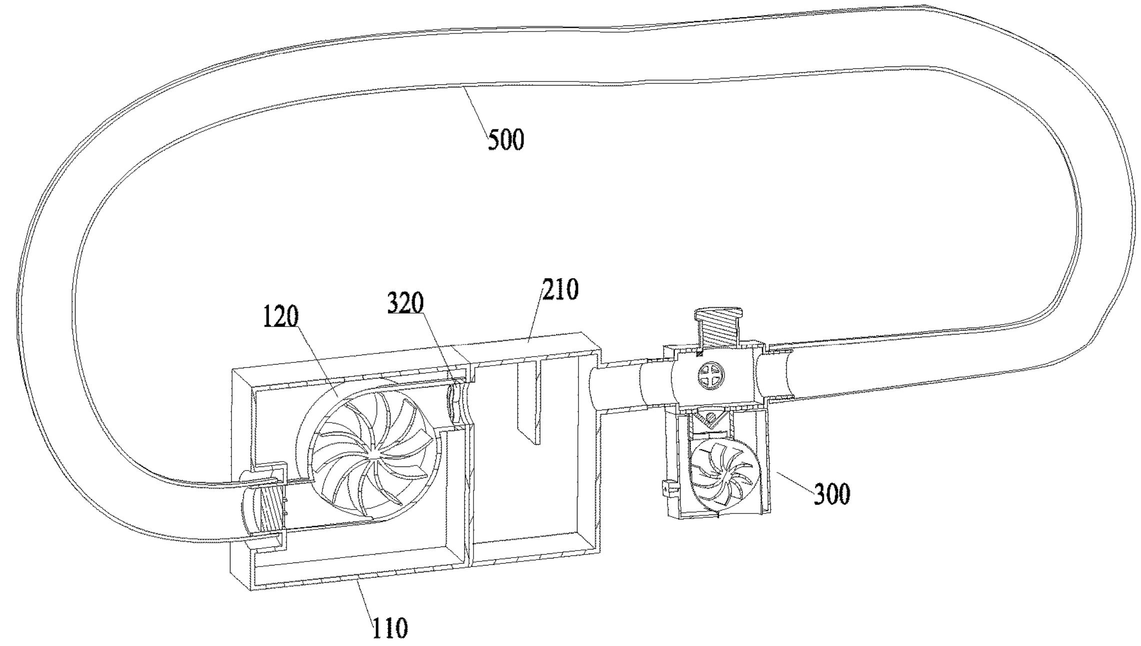
FIG. 16 is a sectional view of yet another embodiment of the ventilation therapy device in the present disclosure.

In the present disclosure, as shown in FIG. 16, the ventilation therapy device may further comprise a disinfection pipeline 500, the two ends of which may be detachably connected to and communicated with the main machine 100 and the disinfection apparatus 300 respectively, so that the disinfection pipeline 500 cooperates with the main machine 100 and the disinfection apparatus 300 to form a channel for the high-temperature disinfecting gas to circulate.

It needs to be noted that the connections between the disinfection pipeline 500 and the main machine 100 and the disinfection apparatus 300 can be direct connections or indirect connections. For example, in the embodiment shown in FIG. 16, the two ends of the disinfection pipeline 500 are directly and detachably connected to the main machine 100 and the disinfection apparatus 300 respectively, specifically, the two ends of the disinfection pipeline 500 are connected to the main machine gas inlet 111 and the transfer case gas outlet 3313; for example, in the embodiment shown in FIG. 9, the two ends of the disinfection pipeline 500 are directly and detachably connected to the main machine 100 and the humidifier 200 respectively (specifically, the two ends of the disinfection pipeline 500 are connected to the main machine gas inlet 111 and the humidifier gas outlet 212), and are indirectly connected to the disinfection apparatus 300.

In addition, to improve the temperature uniformity of the high-temperature disinfecting gas in the entire channel and ensure the disinfection effect, a heating unit 320 may be provided inside the main machine 100, as shown in FIG. 16.

While some preferred embodiments of the present disclosure are described above with reference to the accompanying drawings, the present disclosure is not limited to the details in those embodiments. Those skilled in the art can make various simple modifications and variations to the technical scheme of the present disclosure, without departing from the technical concept of the present disclosure. However, all these simple modifications and variations shall be deemed as falling in the scope of protection of the present disclosure.

In addition, it needs to be noted that the specific technical features described in the above embodiments may be combined in any appropriate form, provided that there is no conflict among them. To avoid unnecessary repetition, various possible combinations are not described specifically in the present disclosure.

Moreover, different embodiments of the present disclosure may also be combined freely as required, as long as the combinations don't deviate from the ideal of the present disclosure. However, such combinations shall also be deemed as being disclosed in the present disclosure.

The invention claimed is:

1. A ventilation therapy device, comprising:

a main machine for generating a therapeutic gas, having a main machine gas inlet and a main machine gas outlet; and a disinfection apparatus for generating a high-temperature disinfecting gas, the disinfection apparatus is communicated with the main machine gas inlet or the main machine gas outlet to introduce the high-temperature disinfecting gas into the main machine, wherein the disinfection apparatus comprises a first power unit, a heating unit, and a gas transfer unit, wherein the first power unit is configured to supply a gas to the gas transfer unit, the heating unit is arranged between the first power unit and the gas transfer unit to heat the gas to form the high-temperature disinfecting gas, and the gas transfer unit is communicated with the main machine, wherein the first power unit comprises a first fan having a first fan gas inlet and a first fan gas outlet; the gas transfer unit comprises a transfer case, which comprises a transfer cavity, a transfer case gas inlet and a transfer case gas outlet that are communicated with the transfer cavity, wherein the transfer case gas inlet is communicated with the first fan gas outlet, the transfer case gas outlet is communicated with the main machine gas outlet or the main machine gas inlet; the heating unit comprises a heating element, which is arranged on a communication passage between the first fan gas outlet and the transfer case gas outlet.

2. The ventilation therapy device of claim 1, wherein the ventilation therapy device comprises a humidifier, which is configured to humidify the therapeutic gas, and has a humidifier gas inlet and a humidifier gas outlet, wherein the humidifier gas inlet is communicated with the main machine gas outlet, and the disinfection apparatus is communicated with the humidifier to introduce the high-temperature disinfecting gas into the humidifier.

3. The ventilation therapy device of claim 2, wherein the gas transfer unit is communicated with the humidifier.

4. The ventilation therapy device of claim 3, wherein the transfer case gas outlet is communicated with the main machine gas outlet and the humidifier gas inlet, or is communicated with one of the main machine gas inlet and the humidifier gas outlet.

5. The ventilation therapy device of claim 4, wherein the first power unit comprises a shell, which comprises a mounting cavity, a shell gas inlet and a shell gas outlet that are communicated with the mounting cavity, wherein the first fan and the heating unit are mounted in the mounting cavity, the shell gas inlet corresponds to and is communicated with the first fan gas inlet, and the shell gas outlet corresponds to and is communicated with the first fan gas outlet and the transfer case gas inlet; and/or wherein the heating unit comprises a mounting cylinder, wherein one end of the mounting cylinder is hermetically connected to the first fan gas outlet, and the other end of the mounting cylinder is hermetically connected to the transfer case gas inlet, and the heating element is mounted in the mounting cylinder.

6. The ventilation therapy device of claim 5, wherein the heating unit comprises a check valve mounted in the mounting cylinder.

7. The ventilation therapy device of claim 3, wherein the main machine comprises a main machine case having a cavity and a second power unit arranged in the cavity, and the main machine gas inlet and the main machine gas outlet are arranged on the main machine case and communicated with the cavity.

8. The ventilation therapy device of claim 7, wherein the second power unit comprises a second fan having a second fan gas inlet and a second fan gas outlet, wherein the second fan gas inlet corresponds to and is communicated with the main machine gas inlet, and the second fan gas outlet corresponds to and is communicated with the main machine gas outlet; and/or the ventilation therapy device comprises a control unit configured to control the operation of the first power unit, the second power unit and the heating unit.

9. The ventilation therapy device of claim 3, wherein the main machine comprises a main machine connector, the first power unit comprises a power connector that is able to be electrically connected to an external power source or the main machine connector to supply power to the first power unit and the heating unit.

10. The ventilation therapy device of claim 2, wherein the ventilation therapy device comprises a throttling unit arranged at the main machine gas inlet and/or the humidifier gas outlet.

11. The ventilation therapy device of claim 10, wherein the throttling unit comprises a throttler configured to be able to connect to the main machine gas inlet or the humidifier gas outlet to throttle the flow rate of the high-temperature disinfecting gas discharged via the main machine gas inlet or the humidifier gas outlet.

12. The ventilation therapy device of claim 10, wherein the throttling unit comprises a protector configured to be able to connect to the main machine gas inlet or the humidifier gas outlet.

13. The ventilation therapy device of claim 2, wherein the humidifier comprises a humidifier shell having a humidifying cavity, and the humidifier gas inlet and the humidifier gas outlet are arranged on the humidifier shell and communicated with the humidifying cavity.

14. The ventilation therapy device of claim 1, wherein the ventilation therapy device comprises a disinfection pipeline, two ends of which are detachably connected to and communicated with the main machine and the disinfection apparatus respectively, so that the disinfection pipeline forms a channel for the high-temperature disinfecting gas to circulate together with the main machine and the disinfection apparatus.

15. The ventilation therapy device of claim 1, wherein the main machine comprises a filter mounted at the main machine gas inlet.

16. A disinfection apparatus, which comprises a first power unit, a heating unit, and a gas transfer unit, wherein the first power unit is configured to supply a gas to the gas transfer unit, the heating unit is arranged between the first power unit and the gas transfer unit to heat the gas to form a high-temperature disinfecting gas, and the gas transfer unit is configured to introduce the high-temperature disinfecting gas into a gas channel of a device to be disinfected, wherein the first power unit comprises a first fan having a first fan gas inlet and a first fan gas outlet;

the gas transfer unit comprises a transfer case, which comprises a transfer cavity, a transfer case gas inlet and a transfer case gas outlet that are communicated with the transfer cavity, wherein the transfer case gas inlet is communicated with the first fan gas outlet, the transfer case gas outlet is communicated with the gas channel of the device to be disinfected; and the heating unit comprises a heating element, which is arranged on a communication passage between the first fan gas outlet and the transfer case gas outlet.

17. The disinfection apparatus of claim 16, wherein the first power unit comprises a shell, which comprises a mounting cavity, a shell gas inlet and a shell gas outlet that are communicated with the mounting cavity, wherein the first fan and the heating unit are mounted in the mounting cavity, the shell gas inlet corresponds to and is communicated with the first fan gas inlet, and the shell gas outlet corresponds to and is communicated with the first fan gas outlet and the transfer case gas inlet.

18. The disinfection apparatus of claim 16, wherein the heating unit comprises a mounting cylinder, wherein one end of the mounting cylinder is hermetically connected to the first fan gas outlet, and the other end of the mounting cylinder is hermetically connected to the transfer case gas inlet, and the heating element is mounted in the mounting cylinder.

19. The disinfection apparatus of claim 18, wherein the heating unit comprises a check valve mounted in the mounting cylinder.

* * * * *